United States Patent [19]

Beach

[11] Patent Number: 5,747,266
[45] Date of Patent: May 5, 1998

[54] ASSAY AND METHOD FOR DETERMINING NEWBORN RISK FOR SUDDEN INFANT DEATH SYNDROME

[76] Inventor: Peter G. Beach, 6780 SW. 205th Ct., Portland, Oreg. 97007

[21] Appl. No.: 710,316

[22] Filed: Sep. 16, 1996

Related U.S. Application Data

[63] Continuation of Ser. No. 100,667, Aug. 2, 1993, Pat. No. 5,556,759.

[51] Int. Cl.$^6$ ............... G01N 33/537; G01N 33/543; G01N 33/564
[52] U.S. Cl. ............... 435/7.9; 435/7.92; 435/7.94; 435/9.75; 436/507; 436/509; 436/513; 436/518
[58] Field of Search ............... 435/7.9, 7.92, 435/7.94, 975; 436/507, 509, 513, 518

[56] References Cited

U.S. PATENT DOCUMENTS

| | | | |
|---|---|---|---|
| 4,332,783 | 6/1982 | Pernice et al. | 435/7 |
| 4,446,233 | 5/1984 | Auditore-Hargraves et al. | 435/7 |
| 4,639,445 | 1/1987 | Moore et al. | 514/282 |
| 4,788,138 | 11/1988 | Tung et al. | 435/7 |
| 4,816,413 | 3/1989 | Sinor et al. | 436/520 |
| 4,829,012 | 5/1989 | Cambiaso et al. | 436/512 |
| 4,844,966 | 7/1989 | Calenoff et al. | 435/7 |
| 4,868,109 | 9/1989 | Lansdorp | 435/28 |
| 4,885,255 | 12/1989 | Stock et al. | 436/512 |
| 4,935,339 | 6/1990 | Zahradnik | 435/5 |
| 5,124,250 | 6/1992 | Inada et al. | 435/7.9 |
| 5,556,759 | 9/1996 | Beach | 435/7.9 |
| 5,583,054 | 12/1996 | Ito et al. | 436/513 |

FOREIGN PATENT DOCUMENTS

0303229  2/1989  European Pat. Off.

OTHER PUBLICATIONS

"Determination of Human Immunoglobuin M. Rheumatoid Factor by a Solid-Phase Radio-immunoassay Which Uses Immunoglobin G in Antigen-Antibody Complexes," Ziola et al., Journal of Clinical Microbiology, vol. 8, No. 2 pp. 134-141 (Aug. 1978).

"Comparative Study of Diagnostic Procedures for Congenital Cytomegalovirus Infection," Stagno et al., Pediatrics, vol. 65, No. 2, pp. 251-257 (Feb. 1980).

"Sudden Unexplained Death in Infancy and Hyperimmunization," Urquhart et al., J. Clin. Path., vol. 24 pp. 736-739 (Feb. 1971).

"A Sandwich Method of Enzyme-Immunoassay, Quantification of Rheumatoid Factor," Maiolini et al., Journal of Immunological Methods, 20, pp. 25-34 (1978).

"Enzyme-Based Methods for IgM Serology: Standard Indirect ELISA vs. Anitbody-Capture ELISA," Wilson et al., Laboratory Medicine, vol. 23, No. 4, pp. 259-263 (Apr. 1992).

"Anti-IgG Binding Test to Assay Circulating IgG-Containing Immune Complexes from Polyethylene Glycol Precipitates," Levinson et al., Clinical Chemistry, vol. 30, No. 9, pp. 1502-1506 (1984).

"The Specificity of Fetal IgM: Antibody or Anti-Antibody?" Reimer et al., Annals of the New York Academy of Science vol. 254, pp. 77-93 (Jun. 30, 1975).

Product literature for "Rheumation Wampole's 2-minute slide test modified Waaler-Rose procedure for the detection of rheumatoid factor (rheumatoid arthritis)," Wampole Laboratories, Stamford, CT 06904.

Harlow & Lane, "Antibodies: A Laboratory Manual," Cold Spring Harbor Laboratory, 1987 pp. 27-28.

Tijssen, P., "Practice and Theory of Enzyme Immunoassays," Laboratory Techniques in Biochemistry and Molecular Biology vol. 15, New York: Elsevier, 1985, pp. 133-136.

Björck L. and Kronvall, G., "Purification and Some Properties of Streptoccal Protein G., a Novel IgG-binding Agent," Journal of Immunology 133 (2) 969-974, 1984.

*Primary Examiner*—David Saunders
*Attorney, Agent, or Firm*—Kolisch, Hartwell, Dickinson, McCormack & Heuser

[57] ABSTRACT

An assay and method for screening newborns to determine risk of Sudden Infant Syndrome is described. The assay and method is based on the detection of elevated IgM-anti-IgG (MAG) levels in newborns' serum within the first year of birth. In particular, it has been discovered that elevated MAG levels indicate an increased risk of Sudden Infant Death Syndrome (SIDS).

2 Claims, 4 Drawing Sheets

ASSAY AND METHOD FOR DETERMINING NEWBORN RISK FOR SUDDEN INFANT DEATH SYNDROME

This is a continuation of application Ser. No. 08/100,667, filed Aug. 2, 1993, now U.S. Pat. No. 5,556,759.

FIELD OF THE INVENTION

The invention relates to newborn diagnostic screening. In particular, the invention involves an assay and method for predetermining the level of IgM-anti-IgG ("MAG") in a newborn's blood, and correlating the MAG level with an empirically determined cut-off to determine whether the newborn has an elevated risk of premature death.

BACKGROUND OF THE INVENTION

Approximately five thousand infants under the age of one die in the United States each year for unexplained reasons, their death ultimately being classified as being caused by "Sudden Infant Death Syndrome" ("SIDS"). The cause of SIDS is not known and no methods for identifying those babies that either have SIDS or are at high risk of developing SIDS, have been previously disclosed.

Prior investigators have suggested that Sudden Infant Death may be related to elevated immunoglobulin concentrations. Urquhart et al., *Sudden Unexplained Death in Infancy and Hyperimmunization*, J. Clin. Path.; 24: 736–739 (Feb. 24, 1971). Urquhart et al. determined postmortem antibody levels in SIDS cases. Urquhart et al.'s studies showed that antiglobulin antibodies were detected in Sudden Infant Death cases more frequently (56%) than in living control cases (5%). Urquhart et al. suggest that anti-antibodies might participate in fatal anaphylaxis in SIDS cases. However, Urquhart et al. did not suggest any technique for identifying newborns who are at elevated risk for SIDS, where the identification can be made at a time early enough to implement measures to prevent premature death.

Various assays have been utilized for quantitating IgM levels. For example, ELISA assays for IgM have been used to diagnose infectious diseases. IgM is a desirable indicator for this purpose because it is generally detectable in the early stages of an infection. These methods employ direct and indirect techniques to quantitate the amount of IgM which is specific for a particular infectious disease related antigen. An objective, when performing IgM assays to detect a specific disease, is to avoid interference from MAG. Wilson et al., *Enzyme-Based Methods for IgM Serology: Standard Indirect ELISA vs Antibody-Capture ELISA*, Laboratory Medicine, Vol. 23, No. 4, Pages 259–263 (April 1992). Thus, ELISAs designed to detect specific infectious diseases do not measure MAG levels, but instead seek to measure antigen specific IgM and to avoid signal generation or interference caused by fluctuating MAG levels.

Assays for a particular type of anti-IgG antibody, namely, relatively high affinity anti-IgG in adults, "rheumatoid factor ("RF"), are used clinically to diagnose or monitor rheumatoid arthritis. Some tests for RF fail to discriminate between MAG and other anti-IgG antibodies such as IgG-anti-IgG and IgA-anti-IgG. Other RF tests specifically detect MAG. For example, a typical test for RF involves preparation of a solid phase with adsorbed human IgG. See Ziola et al., *Determination of Human Immunoglobulin M Rheumatoid Factor by a Solid-Phase Radioimmunoassay Which Uses Human Immunoglobulin G in Antigen-Antibody Complexes*, Journal of Clinical Microbiology, Vol. 8, No. 2, Pages 134–141 (August 1978). However, no one has suggested use of an RF test to detect elevated anti-IgG antibody levels in newborns for the purpose of identifying babies who are at high risk for SIDS. Further, current RF assays are designed to detect relatively high affinity MAG in adults. The RF tests are believed to be inadequate for detecting relatively lower affinity MAG which is typically present in newborns in association with IgG and antigen apparently related to perinatal disease infection.

SUMMARY OF THE INVENTION

Definitions

"MAG" means IgM-anti-IgG.

"SIDS" means Sudden Infant Death Syndrome.

"Binding agent" means a first chemical substance which has specific affinity for a second chemical substance. For example, the first and second chemical substances may be an antibody-antigen pair. A binding agent could also be an antibody which has specific affinity for another antibody. The binding agent could also be a naturally occurring substance such as protein G which has specific affinity for IgG. A binding agent may be naturally occurring or synthetically produced.

"$S_1$" means a baby's relative MAG level determined from a blood sample taken within four days after birth.

"$S_2$" means a baby's relative MAG level determined from a blood sample taken between ten and fifteen days after birth.

"$T_1$" is a point in time between birth and three days after birth.

"$T_2$" is a point in time between ten and twenty days after birth.

Data resulting from my experiments performed on a large number of blood samples collected from infants during their first year after birth shows that more than 90% of the babies who die of SIDS have elevated levels of MAG in their blood after birth. Only 4% of the normal babies tested exhibited such elevated antibody levels. My data supports the hypothesis that the assay I have employed for measuring the levels of MAG in newborns is a valuable tool for, determining whether a newborn is at high risk for SIDS, at a point in time which is early enough to prescribe an appropriate therapy and/or to recommend an observation regimen which can be used to effectively prevent death from SIDS. My invention and all of the data I have generated to validate its efficacy, will also be a valuable tool for the purpose of conducting experiments to gain a greater understanding of what causes SIDS and for the purpose of developing effective therapies or preventative procedures.

The present invention involves a test for determining the level of MAG in a newborn's blood shortly after birth for the purpose of MAG determining the newborn's risk of developing SIDS or other health problems apparently caused by perinatal disease infection.

In a preferred protocol, a blood sample is obtained by collecting a drop of a newborn's blood on a piece of filter paper within four days of birth. At least a portion of the blood sample is contacted with a first binding agent, where the binding agent has specific affinity for IgM antibodies in the sample, under conditions which promote binding between the first binding agent and IgM. A portion of the IgM antibodies which bind to the first binding agent are MAG complexed with IgG. The first binding agent and associated antibodies are then separated from the sample by binding the first binding agent to a solid support and blotting the solid support. The first solid support is then immersed in a solution containing a second binding agent having specific affinity for IgG under conditions which promote release of the IgG antibodies from the first solid support. The second binding agent is preferably conjugated to a detection element or substrate such as a fluorophore, an enzyme or a radio labeled compound. For example, in a preferred embodiment the second binding agent is conjugated to peroxidase. The second binding agent and associated IgG is then separated from the remaining solution and constituents by contacting the solution with a second solid support on which a third binding agent having specific affinity for IgG is adsorbed. After sufficient time has passed to allow the IgG antibodies to bind to the second solid support, the second solid support is removed from the solution and washed.

Finally, the amount of second binding agent present on the second solid support is quantitated by contacting the second solid support with a buffer containing O-phenylenediamine or another appropriate chromogen which changes color in response to the production of hydrogen peroxide, the production of which is catalyzed by the peroxidase enzyme. The rate of color change, which can be monitored by a spectrophotometer at a designated wave length, directly correlates with the quantity of peroxidase, i.e., second binding agent bound to the second solid, support. The amount of second binding agent on the second solid support correlates to the amount of IgG which was removed from the sample via the first solid support, which is directly related to the quantity of MAG in the baby's blood. The MAG level is then correlated with a normal distribution. Babies who exhibit MAG levels in the top 4% relative to the normal distribution are classified as being at high risk for SIDS.

In the method of the present invention, the sampling time is important. It appears that elevated MAG levels in SIDS babies are sometimes a result of congenitally contracted diseases, and that other SIDS babies produce elevated MAG levels as a result of neonatally contracted diseases. For those SIDS babies which were congenitally infected, the preferred time for sampling is within four days after birth. For SIDS babies which appear to be infected after birth, the preferred time for testing is between ten and fifteen days after birth. Therefore, it is recommended to sample and test the baby's blood multiple times during the first year after birth. In particular, the baby's blood should be sampled and tested within four days after birth ($T_1$) and again between ten and fifteen ($T_2$) days after birth.

DETAILED DESCRIPTION OF THE PREFERRED EMBODIMENTS

Figure 1:
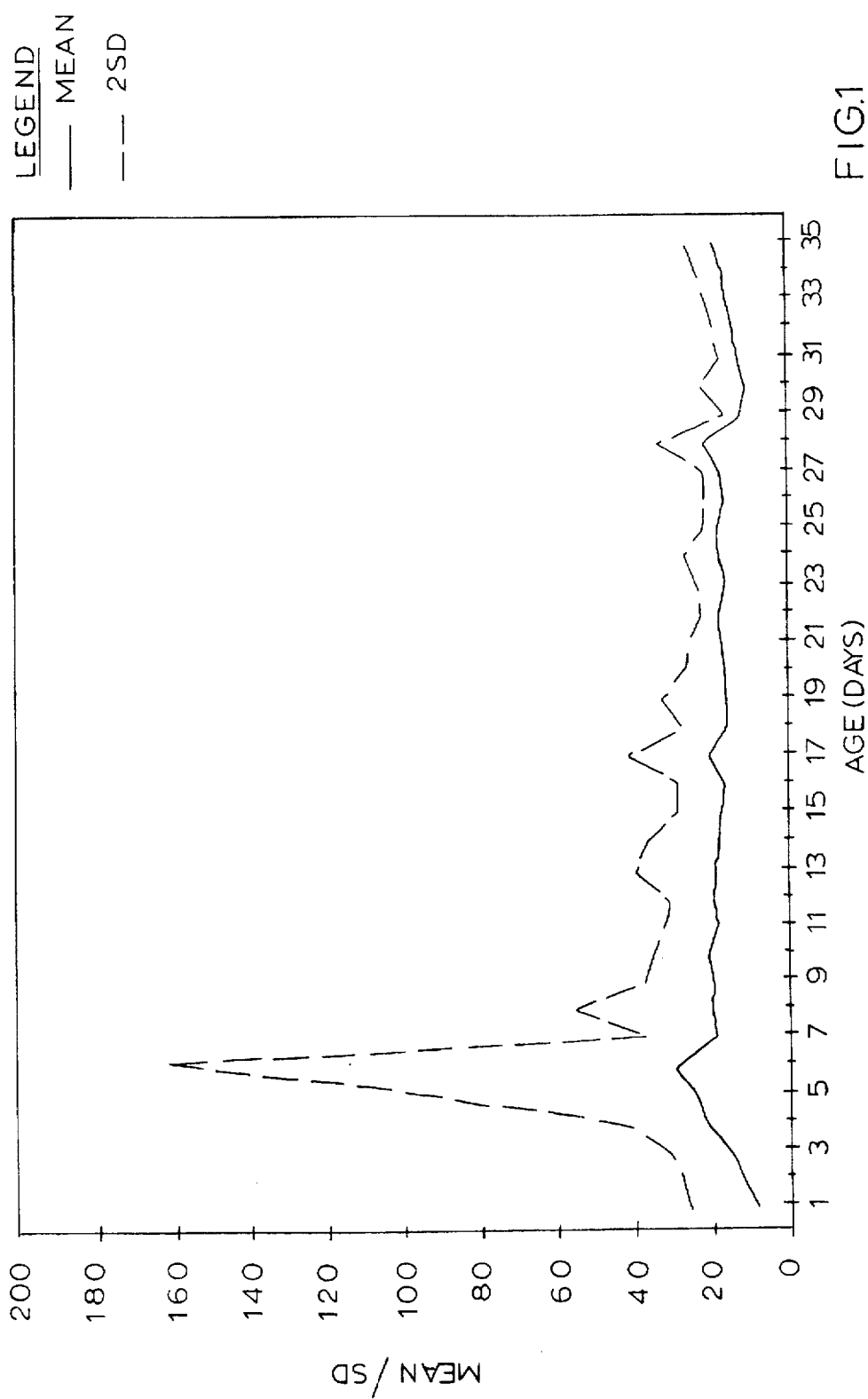
FIG. 1 is a graphical plot showing the mean and standard deviation of MAG levels in newborns as a function of sampling time.

A preferred assay and method of the present invention involves quantitation of MAG and associated IgG in a newborn's blood shortly after birth for the purpose of determining whether the newborn is at elevated risk for SIDS. The assay utilizes at least two specific binding agents, the first having specific affinity for IgM and the second having specific affinity for IgG. Solid support adsorption and washing procedures are used to separate the specific binding agents and associated analytes from the other blood constituents.

In a preferred assay embodiment of the present invention the following materials are used. Plates A and B are 96 "U" shaped well plates. Plate B and a beaded cover have surfaces adsorbed with GX avidin. Plate B wells are secondarily adsorbed with biotinylated protein G. All solid supports are blocked, for example with silicone or BSA. Buffer 1 is a PIPES buffer with biotinylated goat anti-human-IgM. Buffer 2 is a PIPES buffer with peroxidase conjugated Protein G (recombinant). Buffer 3 is a dilute PIPES buffer used as a wash. Buffer 4 is a PIPES buffer with o-phenylenediamine, mixed just before use. The buffers do not contain antibacterial agents.

Buffer 1 is specifically formulated for optimum MAG-IgG complexing. The pH, 6.8±0.2 was selected to minimize hemoglobin interference. The PIPES buffer was selected because it has a buffering range consistent with the required pH under the conditions of the test, but any combination of buffers used in this pH range could be used. PIPES was also selected because it has minimal chelating characteristics which appears to be important. Magnesium ion has been found to help stabilize the complex. In addition, PIPES does not require a chlorinated acid/base mixture to achieve the required buffering capacity. The exclusion of chlorine ion from the buffer was found to improve the test. No protein or carbohydrate stabilizer/blocking of antibacterial agents are in the buffer, but the buffer was designed to allow for the addition of specific antigens which may be helpful to enhance the sensitivity and specificity of the test.

A preferred method of the present invention includes the following steps. Plate A is removed from its protective cover (at room temperature). Blood spots consisting of a paper punch taken from drops of babies blood collected at $T^1$ and $T_2$ and other times within one year after birth and dried on a piece of filter paper, are dropped into the wells of plate A according to a predetermined order, including controls and standards.

250 lambda of buffer 1 is added to each well, giving approximately a 1:200 dilution of the eluted blood spot.

Plate A is loosely covered and rotated at 90 RPM for one hour at 24° C.±2° C. Floating spots are immersed at the end of one hour and the elution procedure is repeated. At the end of the second hour of elution, the eluate is mixed thoroughly at room temperature with a multichannel pipettor. A volume of 125±25 uL works well. The eluate fluid is drawn in and out approximately six times. The use of avidin and biotin in this test are not mandatory. Other methods of binding solid phase antibodies to a solid support with low background and low desorption may also be used. The pipet tips are then changed and the process is repeated for each row of wells.

The plates are then covered with beaded cover plates and incubated in a closed moist chamber for five days at 4° C. A one or two day incubation period causes the test to be less sensitive. One and two day incubations are less sensitive with respect to those infants with marginal amounts of low avidity MAG. Fresh blood spots are used for all repeat tests.

Incubate for five days (120±8 hours) at 4° C.±2° C.

Fifteen minutes prior to removing the plates from cold incubation, plate B is set up and preincubated with 300 lambda of buffer 2 in each well at 45° C.±2° C. by floating the plate in a closed waterbath.

The beaded cover is removed from plate A, blotted and moved to plate B. The plate and beaded cover are gently bumped while floating in an incubation chamber at 45° C. for two hours. It is important that the beaded cover be blotted instead of washed so that even the low affinity MAG will facilitate transfer of IgG from the sample to plate B. This is different from the typical ELISA or MAG which washes away low affinity MAG before detecting the quantity of MAG bound to a solid support.

It may also be advantageous to dope antigen into buffer 1 so that the capture of MAG and associated IgG is not antigen dependent. Otherwise, MAG will typically not bind to IgG unless the IgG is complexed to antigen originating from the sample or unless the IgG is kinked for some other reason.

The beaded cover is removed from plate B. A semiautomatic or automatic plate washer is used to wash the wells of plate B three times with wash buffer 3. Buffer 3 is preferably 24° C.+20 C. Plate B is allowed to sit for approximately 30 to 60 minutes to equilibrate to room temperature before proceeding.

300 lambda of Rx buffer 4 is added and plate B is incubated for one hour at 24° C.±2° C.

A stop reaction solution such as 1N $H_2SO_4$ is added. The color developed in each well is read in an automatic or semiautomatic plate reader at the appropriate wavelength.

The presence or absence of neonatal MAG determined by relating the adsorbance value of the specimen to the cutoff value calculated from the standards used. Each EIA kit has its own parameters for calculating the cutoff value.

Specimens are classified as reactive or nonreactive (positive or negative) by calculating the MAG value and comparing it to the cutoff MAG value.

Nonreactive specimens have adsorbance values less than the, cutoff value. They are considered negative for IgM anti-IgG and further testing is not required.

Reactive specimens have adsorbance values equal to or greater than the cutoff value. They are considered reactive candidates and should be retested in duplicate before declaring serostatus of the specimen. If one or both repeat tests are reactive, the specimen is considered a confirmed reactive. If both repeat tests are nonreactive, the specimen is declared nonreactive.

The assay described above is referred to as "the capture assay" because it involves "capture" of MAG, IgG and antigen complex from the sample for transfer into a second buffer. An alternative to the capture assay, details of which are described below under "materials and methods", is referred to as the "sandwich assay" because it involves the use of an antibody-antigen-antibody sandwich on a solid phase. In the sandwich assay employs a microtiter well which has been previously adsorbed with gamma-globulin. In a first incubation step any anti-globulin in the sample binds to the solid phase. The solid phase is washed and an anti-IgM enzyme conjugate is added and allowed to bind to MAG which is bound to the solid phase via gamma-globulin. After washing, a chromogen solution is added in order to quantitate the amount of enzyme conjugate bound to the solid phase, thus indicating the amount of MAG in the sample.

Other modifications of the capture assay and/or the sandwich assay can be used in the present invention. For example, in a "modified capture technique" an antigen is provided in the first buffer. For example, use of disrupted purified cytomegalovirus (CMV) viral constituents, will allow unreacted anti-CMV IgG to react with CMV antigen, potentiating reaction of CMV IgG with MAG. In addition, a label such as a radioactive, fluorescent, or enzyme moiety can be conjugated to the antigen. The labeled antigen becomes part of the immune complex that is brought from the first buffer to the second buffer. Once the anti-CMV IgG or other anti-antigen IgG is bound to the second solid matrix on the second plate, the complex is identified by direct application of chromogen. This technique avoids the necessity for the step of adding enzyme linked anti-IgG or protein G. Thus, the modified capture technique tests indirectly for MAG but also provides information about the specificity of the IgG antibody that reacts with MAG. If a particular antigen is identified as being commonly involved in SIDS, this could create an even more sensitive and specific assay. The use of mixtures of different viral antigens could be used if other viral infections were found to be involved in SIDS.

One way to produce a labeled CMV antigen for use in the modified capture technique is to biotinylate a CMV viral constituent, and provide enzyme conjugated avidin in the second buffer. As the IgG-CMV-biotin complex is bound to the second plate, the avidin-enzyme reacts with the biotin creating a styrene plate-protein G-IgG-CMV-biotin-avidin-enzyme complex on the second plate. The plate is washed three times and chromogen added. The test will exhibit improved sensitivity due to there being more than one biotin molecule on the CMV/viral antigen. The extra number of avidin-enzymes attached will amplify the signal, providing increased sensitivity.

Experimental Examples

The sandwich assay was used in experiments 1–4 below. The capture assay was used in experiment 5.

Materials and Methods

Microtiter Plates were 96 well polystyrene plates with "U" shaped wells (Falcon). Plate sensitization was accomplished with 600 uL aliquots of 10 mg/100 mL rabbit gamma-globulin, Cohn fraction II (Sigma) in 0.1M carbonate buffer pH 9.6. Six hundred uL aliquots of a 15 g/100 mL glycine solution in 0.1M carbonate buffer pH 9.6, was used as a blocking agent. The plates were covered and incubated at 4° C. overnight. The plates were then washed one time with 0.01M carbonate buffer pH 9.6 with the flood and dump method, shaken dry, and used within two hours. Plates were covered until used. The elution buffer was composed of 8 g/100 mL BSA (Sigma), 0.8 g/100 mL glycine (Sigma), 2.6 g/100 mL NaCl, 2 mL/100 mL DMSO (Sigma), and brought to pH 7.8. The second antibody buffer was composed of 0.05M TRIS-HCL pH 8.0 (Sigma), anti-human IgM (goat) peroxidase conjugated antisera, diluted 1:1000 v/v (Dynatech), and 1 g/100 mL BSA (Sigma). The chromogen solution was composed of 97 mL, diethanolamine (Sigma), 900 mL water, 100 mg $MgCl_2$ $6H_2O$, pH 9.8, brought to a total volume of 1 liter and stored at 4° C. in the dark. One hour prior to use, this solution was brought to room temperature and 1 mg/100 mL O-phenylenediamine dihydrochloride (Sigma) was mixed into solution. Just prior to use, 0.3 mL of 3% hydrogen peroxide was added.

Newborn heel, stick specimens, dried on Schleicher and Schuell #903 filter paper were collected. Specimens were received, processed and stored daily in air tight plastic bags at 4° C. up to one week and −20° C. for up to one year before testing.

The positive serum used for the standards was from a patient with systemic lupus erythematosus and had a latex titer of approximately $1:10^6$ IU. Packed human type 0 red blood cells were mixed 1:1 with diluted standards, blotted on filter paper and allowed to dry before use. The five standards were 320, 80, 20, 5 and 0.1 units.

The plates were given a plate number and a work sheet was created. Using a 3mm paper punch (Gem, McGill Co., Marengo, Ill.), one punch of 3mm diameter was taken from each standard and unknown and added to each well. The elution buffer was then added to the spots, 300 lambda/well using a semiautomatic dispenser. The plates were covered to prevent excessive evaporation. The plates were then placed on a rotator for 5 minutes and checked for spots that are not sinking. A metal probe was used to force air bubbles from the spots. The plates were then recovered and placed on the rotator and incubated at room temperature for 2 hours. Following this incubation, all plates were incubated overnight (16–20 hours) at 4° C.

Following overnight incubation, the microtiter wells were washed 3 times with elution buffer minus BSA, using the flood and dump method. The plates were shaken gently to remove excess buffer. The second antibody buffer was then added, 250 uL/well, with a semiautomatic dispenser. The plates were then incubated at room temperature for 1 hr. Following incubation, the plates were washed 3 times with elution buffer minus BSA, using the flood and dump method. The plates were then shaken gently to remove excess buffer. The OPD chromogen solution was then added, 250 uL/well with a semiautomatic dispenser and incubated at room temperature for one hour or until the highest standard was about 1.000 OD. The plates were read within one minute with a manual OD reader (Litton, Bionetics) at 410 nm.

EXPERIMENT 1

Intratest Reproducibility:

The five standards were tested eight times in one plate. The results were analyzed using raw optical density readings. There was no negative standard due to the difficulty of finding human sera with no MAG titer.

The intratest reproducibility results are shown in Table I. The test results of the five standard specimens demonstrate a test with coefficients of variation from 10.1 to 15.8. Linear regression of the means of the five standards resulted in a slope of 1.12 and correlation coefficient of 0.98. These results indicate a test with adequate reproducibility characteristics for comparisons within a daily run.

TABLE I

| | Intratest Reproducibility | | | | |
|---|---|---|---|---|---|
| | 0.1 units OD | 5.0 units OD | 20.0 units OD | 80.0 units OD | 320 units OD |
| | 0.249 | 0.282 | 0.370 | 0.439 | 0.590 |
| | 0.309 | 0.224 | 0.317 | 0.307 | 0.505 |
| | 0.206 | 0.240 | 0.312 | 0.316 | 0.445 |
| | 0.202 | 0.259 | 0.225 | 0.320 | 0.493 |
| | 0.224 | 0.226 | 0.257 | 0.332 | 0.538 |
| | 0.236 | 0.257 | 0.355 | 0.360 | 0.598 |
| | 0.232 | 0.305 | 0.334 | 0.353 | 0.545 |
| | 0.231 | 0.332 | 0.345 | 0.378 | 0.590 |
| N | 8 | 8 | 8 | 8 | 8 |
| MEAN | 0.236 | 0.266 | 0.314 | 0.351 | 0.538 |
| SD | 0.033 | 0.038 | 0.050 | 0.043 | 0.055 |
| CV | 14.1 | 14.4 | 15.8 | 12.3 | 10.1 |

Table I shows the linear regression of means; slope=1.12, intercept=0.235, correlation coefficient=0.98.

EXPERIMENT 2

In this experiment I compared MAG test results of 1,646 newborn specimens with respect to age of the newborn at time of specimen collection. The age of these newborn infants at time of specimen collection varied from 1 to 35 days. The specimens were collected over a two week period in order to adequately represent each age group. In addition, 47 normal adult, 61 SIDS and 34 cohort blood spot specimens were tested. The results were quantified, using standards equivalent to the intratest reproducibility experiment.

The distribution of MAG titers, for the infants, as shown in Table II, showed a low point on the first day following birth (mean=157, N=63) and a peak on the fifth day following birth (mean=454, N=146). By the fifteenth day following birth there is a leveling of MAG values approximately 50% below the maximum newborn mean (310 vs 454 units) and the normal adult mean (310 vs 439 units).

TABLE II

The Distribution of IgM anti-IgG in Newborn Blood Spot Specimens and Age

| AGE (Days) | N | Mean | SD |
|---|---|---|---|
| 1 | 63 | 157.4 | 177.5 |
| 2 | 177 | 220.8 | 283.6 |
| 3 | 188 | 279.6 | 144.1 |
| 4 | 200 | 373.8 | 378.0 |
| 5 | 146 | 454.2 | 663.2 |
| 6 | 139 | 395.0 | 142.5 |
| 7 | 82 | 311.8 | 130.5 |
| 8–14 | 288 | 342.7 | 188.8 |
| 15–21 | 211 | 297.8 | 133.4 |
| 22–28 | 83 | 309.5 | 72.5 |
| 29–35 | 69 | 302.1 | 92.3 |
| | 1,646 | | |

47 normal adult specimens had a mean titer of 439 units, SD 366. The cohort specimens had approximately the same mean age (2.5 days, SD 2.4) as the SIDS infants (2.8 days, SD 3.8). The 34 cohort specimens had a mean MAG titer of 318 units, SD 160. The 61 SIDS infants had a mean MAG titer of 474 units, SD 192.6.

The mean and standard deviations of newborn MAG levels is plotted against newborn age (days) in FIG. 1. The graph shows a high level of variability in MAG levels between five and seven days after birth, demonstrating the importance of obtaining a sample from the newborn within the first four days after birth.

Figure 2:
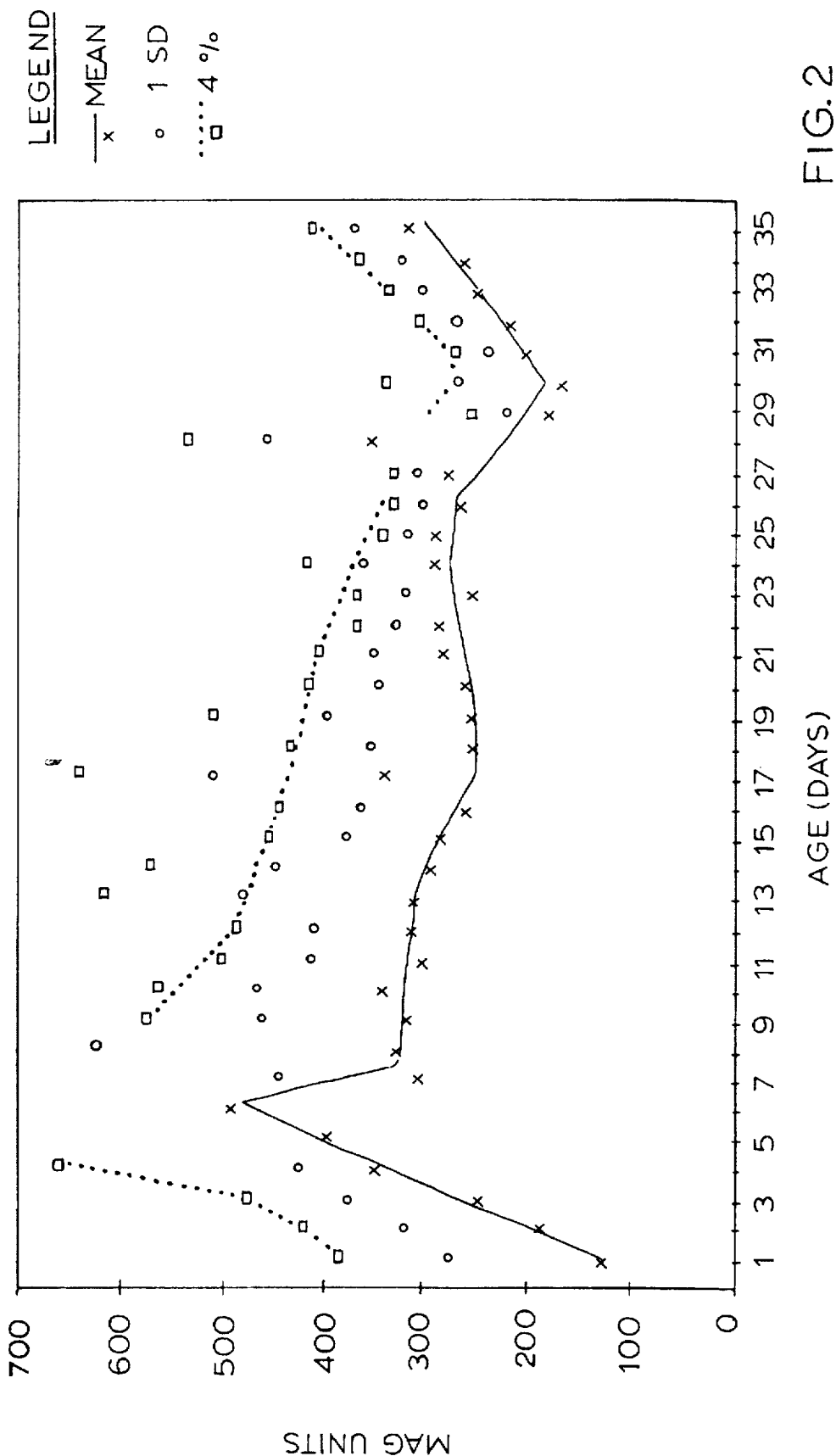
FIG. 2 is a graphical plot comparing MAG levels for normal newborns verses MAG levels for SIDS babies as a function of the time of sampling.

FIG. 2 shows MAG units as a function of sample time. The solid line represents the mean MAG value in a normal population. The dashed line represents the cut-off which separates the individuals having the top 4% of MAG values from the rest of the newborn population.

EXPERIMENT 3

The third experiment, conducted six times (tests I–VI), was unblinded using SIDS and cohort infant specimens tested in pairs or groups of one SIDS specimen and two cohort specimens. No SIDS/cohort group was counted more than once.

In these experiments, cohort specimens were selected in two manners. The first method, used in tests I, IV, V and VI, was to select cohort blood spot specimens from newborns who most closely resembled the SIDS infants based upon information on the Newborn Screening forms, part of the specimen collection kits. Cohorts were selected according to the following criteria:

(1) Cohorts were within one pound of birth weight (an approximately equal number of cohorts with birth weights higher and lower than the SIDS infants). (2) Cohorts' birth dates were the same day plus or minus one day. (3) The infants' ages at time of specimen collection with a few exceptions were within one day in age of each other. If the SIDS infant specimen was drawn at an age where there were few cohort specimens to select from, considering all other criteria, the specimen was chosen from the next closest age.

(4) Cohorts were the same sex. (5) Cohorts' specimens were received and processed on the same day, with the few exceptions mentioned in 3. SIDS and cohort specimens were handled and stored as similarly as possible.

The second method by which cohort specimens, used in tests II and III, were selected was to select specimens which came chronologically just before and or after the SIDS infant specimen. This method disregarded all criteria used in the first method, however due to program sorting criteria these pair/group specimens were almost exclusively the same patient age at time of collection. In group II, eleven cohort specimen pairs were both preceding and following the SIDS specimen, with another six only preceding and five only following the SIDS specimen. The only reason a specimen was not used was based upon specimen unavailability. In group III, only pairs of cohort specimens were chosen, one preceding and one following the SIDS infant specimens. No attempt was made to check for introduced bias, other than age at time of collection, but what bias might have been introduced was probably not systematic.

Test results (delta O.D.) were computed by subtracting the background optical density reading for each plate from the optical density reading of the unknowns. The MAG test results for the six groups of SIDS and cohort infant specimens, as shown in Table III, show that the mean delta OD values of SIDS specimens is generally higher than their cohort(s). However, there is considerable overlap in these test results.

TABLE III

Comparison of SIDS and Cohort IgM anti-IgG Test Results

| | Group Number | I | II | III | IV | V | VI | Total |
|---|---|---|---|---|---|---|---|---|
| | N | 22 | 20 | 10 | 14 | 20 | 22 | 108 |
| SIDS | delta OD | 39 | 75 | 32 | 75 | 61 | 109 | |
| | SD | 78 | 89 | 69 | 86 | 76 | 115 | |
| | N | 22 | 31 | 20 | 14 | 20 | 22 | 129 |
| Cohorts | delta OD | 26 | 26 | 0 | 23 | 48 | 95 | |
| | SD | 56 | 110 | 35 | 85 | 80 | 137 | |

Table III shows the test results of Experiment 3. Mean delta OD values were higher for SIDS infants in all six experiments. However, there was considerable overlap of SIDS and cohort delta OD values.

Using the same raw data from Experiment 2, a comparison of the SIDS and cohort test results, using signs, is shown in Table IV. Sixty-five percent (71/110) of SIDS specimens had higher delta OD values than their cohorts. Using a Z test of significance, Z=3.0 SD, showing a very significant difference between the SIDS and cohort specimen MAG values.

TABLE IV

Signs Comparison of SIDS and Cohort Test Results

| Group Number | I | II | III | IV | V | VI | Total |
|---|---|---|---|---|---|---|---|
| N | 22 | 20* | 11* | 14 | 20 | 23 | 110 |
| SIDS delta OD test results higher than cohort/controls | 12 | 15 | 7 | 11 | 14 | 12 | 71 |
| SIDS delta OD test results lower than cohort/controls | 9 | 5 | 3 | 2 | 6 | 11 | 36 |
| SIDS and cohort/control test results tied | 1 | 0 | 1 | 1 | 0 | 0 | 3 |

*Most of these test pairs had more than one cohort, different combinations were tried. These results are representative of each group.

Table IV compares the delta OD values of SIDS and cohort test results. Using a Z test of significance, Z=3.0 SD, demonstrating a very significant difference between the SIDS and cohort test results.

EXPERIMENT 4

This pair of experiments included the screening of 333 and 462 Oregon newborn blood spot specimens, respectively, processed in accession number order, from daily newborn screening runs. Retrospectively, SIDS death certificate data was analyzed two years after the first and one year after the second screening was conducted. SIDS infants born in the general time frame of the screenings were compared to the demographic data on the newborn screening form. The data from three SIDS infants matched in last name, birth date, sex, birth weight and hospital of birth. All other SIDS infants in the general time frames of the screenings were matched to newborn screening specimens, accounting for all candidate SIDS infants.

This set of experiments incorporated units of measure for general comparison to the MAG test results of experiment 2. The unit value for these specimens was determined by subtracting background OD from the raw OD value and then multiplying by a constant. The two constant values were chosen to match the combined mean titers of the three age groups of each screening with the combined mean titers of the 1-3 day age group from experiment 1. The results of the third experiment, two retrospective studies of a total of 759 blood spot specimens from newborns are shown in Table V. Specimens from newborns with matching ages, at time of collection, were compared with one exception. In the second screening, the specimens collected on the first day and second day were inadvertently and irreversibly combined. This complication, however, did not adversely effect the results of this experiment because the SIDS infant specimen in that screening had the second highest value found in that combined age group. Since no SIDS infant specimen in either screening was collected more than three days after birth, only age groups one through three days were evaluated. Three SIDS deaths coincided with these two screenings and all three were tested in the screenings.

One SIDS infant was detected in the first screening. This specimen was drawn on the second day following birth, with a calculated MAG titer of 514 units. The mean value of this age group was 195 units, SD=184. The four other specimens in the top 4%, N=122, had 578, 551, 547 and 507 MAG units. A second SIDS infant was detected in the second screening. This specimen was drawn on the first day following birth, with a calculated MAG titer of 544 units. The mean value of this age group was 219 units, SD=87. A third SIDS infant was not detected in the second screening and had a MAG titer of 145 units and was drawn on the third day following birth. The mean MAG titer of this age group was 253 units, SD=140. The seven other specimens in the top 4%, N=203, had 770, 411, 411, 405, 400, 400 and 394 MAG units.

TABLE V

Two Mass Screening Test Results

| | Age at Collection | Mean | SD | N | SIDS Specimens | SIDS Top 4% | Total Top 4% |
|---|---|---|---|---|---|---|---|
| First Screening | 1 day | 234.6 | 167.0 | 96 | 0 | 0 | 4 |
| | 2 days | 195.0 | 184.2 | 122 | 1 | 1 | 5 |
| | 3 days | 237.1 | 184.5 | 115 | 0 | 0 | 5 |
| | | | | 333 | 1 | 1 | 14 |
| Second Screening | 1–2 days | 218.7 | 87.1 | 203 | 1 | 1 | 8 |
| | 3 days | 253.3 | 139.5 | 259 | 1 | 0 | 10 |
| | | | | 462 | 2 | 1 | 18 |
| | | Totals | | 795 | 3 | 2 | 32 |

Initially, as shown by the data in Table V, I discovered that most SIDS babies have $S_1$ MAG levels in the top 4% of all babies tested. It appeared that the elevated $S_1$ MAG 30 levels were due to congenitally contracted diseases. I later discovered that some of the SIDS babies did not have $S_1$ MAG levels in the top 4% ("a negative S test") but did have a positive S2 test based on blood samples collected at $T_2$. I now believe that the babies who have negative $S_1$ MAG levels, but later develop positive $S_2$ MAG levels are neonatally infected. Regardless of whether my hypothesis regarding infection is correct, by using my test to determine $S_1$ and $S_2$ MAG levels I can pick out over 90% of SIDS babies with a small number of false positives.

Figure 3:
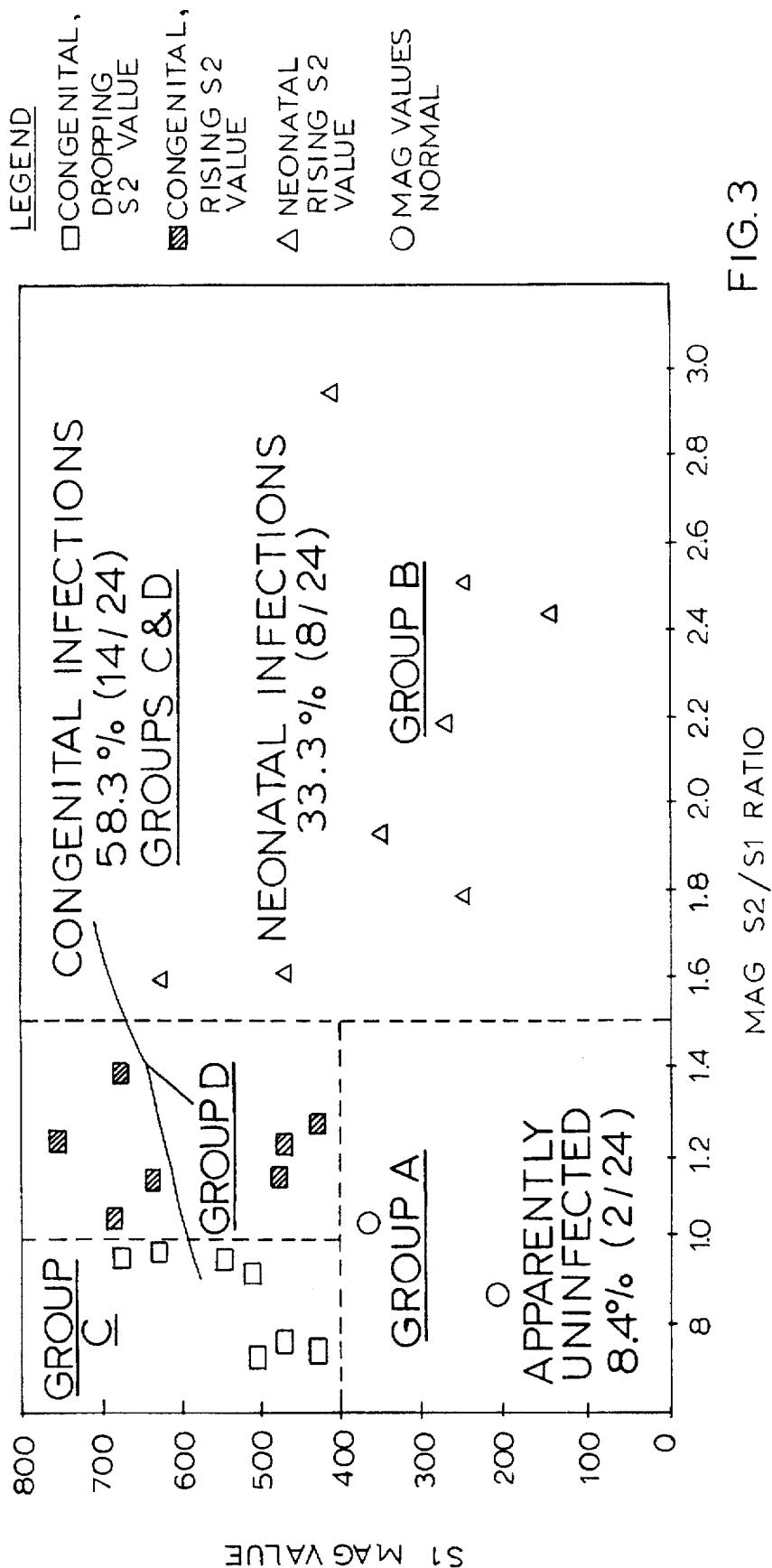
FIG. 3 is a graphical plot comparing $S_1$ MAG values for SIDS babies as a function of $S_2/S_1$ ratios.

I then identified 24 SIDS infants, i.e., infants who had died, from whom blood samples had been previously collected and retained, each of whom had given a blood sample at $T_1$ and $T_2$. For each of the 24 SIDS infants I determined their $S_1$ MAG level and $S_2$ MAG level. As shown in FIG. 3, I then grouped the SIDS infants according to their $S_1$ MAG value and the ratio of their $S_2$ MAG level to their $S_1$ MAG level. The graph in FIG. 3 is portioned into four parts. Group A represents 2 of the 24 SIDS infants (8.4%) who had negative $S_1$ MAG levels and whose MAG ratio ($S_2/S_1$) did not increase significantly. The SIDS infants in group B include those babies whose MAG ratio is greater than 1.5. At least 5 of the 8 babies in this group had negative $S_1$ values but developed substantially higher $S_2$ MAG levels. Group C includes 7 of the 24 SIDS babies each of whom had a positive $S_1$ value and a smaller $S_2$ MAG level. Group D includes 7 of the 24 SIDS infants each of whom had a positive $S_1$ value and experienced a rising blood MAG concentration through $T_2$.

Figure 4:
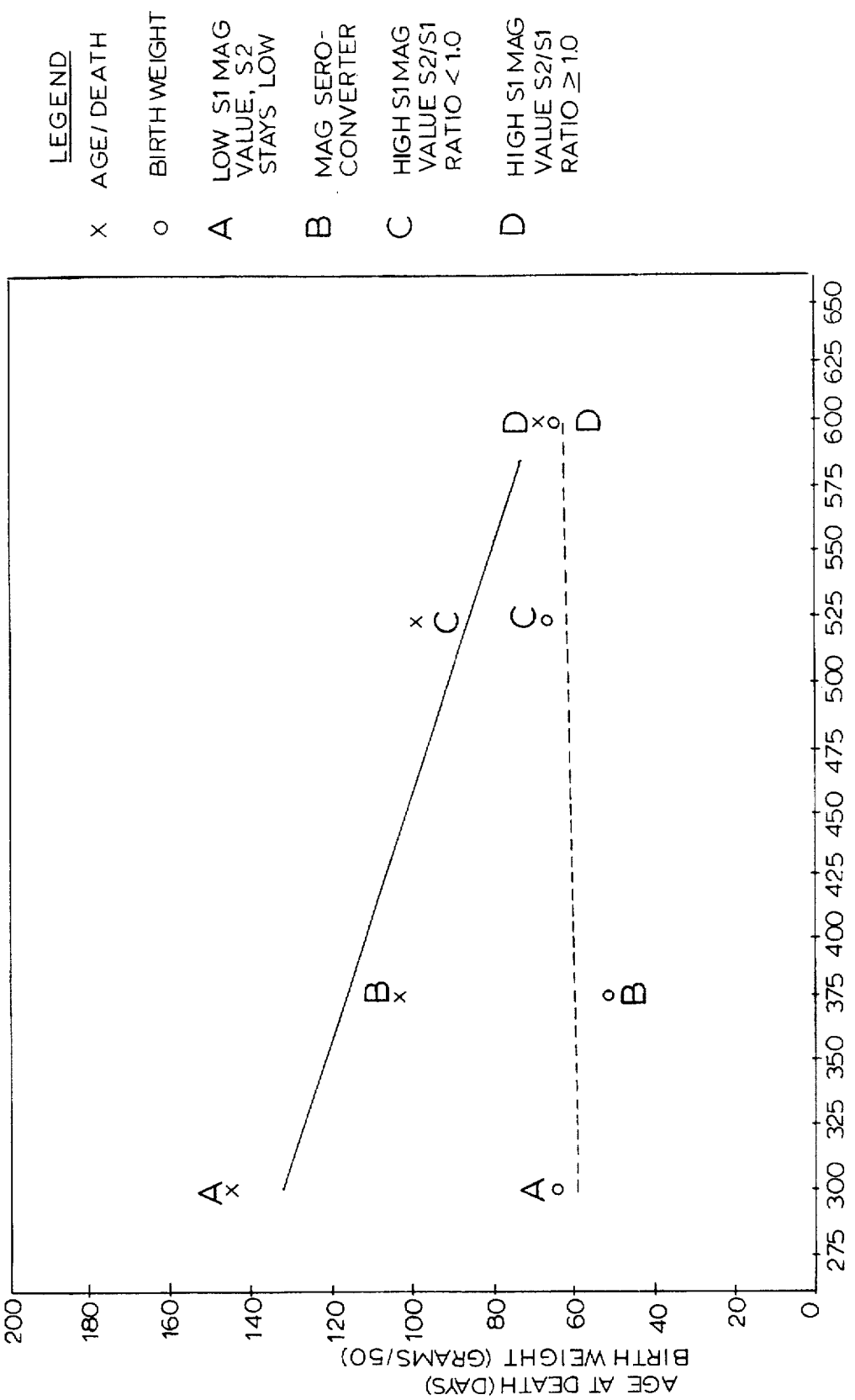
FIG. 4 is a graphical plot comparing the age of death for SIDS babies as a function of $S_1$ MAG values.

FIG. 4 shows the average $S_1$ MAG values for each of the groups A–D as a function of the average age of death for each group. The average age of death for babies in group D, i.e., those babies whose MAG levels started out high and increased, was less than the average age of death for the other groups. The babies in group C, i.e., those babies who started out with high MAG levels but whose MAG levels did not increase through $T_2$, had the second lowest average age of death. Group B, i.e., those babies most of which started out with negative $S_1$ MAG values, but whose MAG levels increased significantly through $T_2$, had the second to the highest average age of death. Finally, the babies in group A, i.e., those babies who produced negative $S_1$ and $S_2$ MAG levels, had the highest average age of death. It is possible that the 2 babies in group A developed high MAG values after $T_2$. However, samples were not available for testing.

EXPERIMENT 5

In this experiment I compared delta OD values for ten SIDS babies with ten cohort babies. The delta OD values were generated by the capture assay described above. The results are shown below in Table VI.

TABLE VI

Comparison of SIDS and Cohort MAG Capture Test Results

| | Group Number | I | II | Total |
|---|---|---|---|---|
| SIDS | N | 4 | 6 | 10 |
| | delta OD | .836 | 1.173 | |
| | SD | .102 | .349 | |
| Cohorts | N | 4 | 6 | 10 |
| | delta OD | .730 | 1.068 | |
| | SD | .198 | .243 | |

Table VI shows that mean delta OD values were higher for SIDS infants in both experiments. As was expected, there was overlap in SIDS and cohort delta OD values. The sum difference between SIDS and cohort delta OD values using the MAG sandwich was approximately +0.029 OD. The sum difference between SIDS and cohort delta OD values using the MAG capture technique was approximately +0.105 OD. The ratio of differences in SIDS and cohort delta OD values is three to four times greater than with the MAG sandwich technique, i.e., 0.105/0.029=3.61.

Using signs comparison, SIDS infant delta OD values were higher than cohort values in three of four SIDS/cohort pairs in group I and four of six in group II. Therefore, seven of ten SIDS delta OD values were higher than cohorts using the MAG capture technique. This is comparable to the MAG sandwich technique.

The preferred assays and protocols described above may be modified within the spirit and scope of the invention, as claimed below.

I claim:

1. An assay kit for detecting the quantity of a newborn baby's IgM-anti-IgG (MAG) comprising:
    a first binding agent having specific affinity for IgM;
    a first solid support treated so that it adsorbs the first binding agent and associated IgM;
    a second binding agent having specific affinity for IgG; and
    a detection mechanism for determining the quantity of second binding agent bound to IgG, wherein the detection mechanism includes a second solid support having a surface and a third binding agent bound to the surface of the second solid support, the third binding agent having specific affinity for IgG.

2. A method for determining whether a newborn is at high risk for SIDS comprising the steps of:
    collecting a blood sample from the newborn within four days of birth
    quantifying the amount of IgM-anti-IgG (MAG) in the sample by:
        contacting IgM from the sample with a first binding agent having specific affinity for IgM under conditions which promote binding between IgM and the first binding agent, wherein a portion of the IgM bound to the first binding agent is MAG complexed with IgG;

separating the first binding agent with associated IgM and IgG from the other blood sample constituents;

measuring the quantity of IgG separated from the sample, thereby indirectly indicating the quantity of MAG in the sample; and correlating the MAG level with standards to determine the newborn's risk for SIDS.

* * * * *